United States Patent [19]

Carr et al.

[11] Patent Number: 4,912,117

[45] Date of Patent: Mar. 27, 1990

[54] NOVEL CHEMICAL COMPOUNDS

[75] Inventors: Albert A. Carr; Norbert L. Wiech, both of Cincinnati, Ohio

[73] Assignee: Merrell Dow Pharmaceuticals Inc., Cincinnati, Ohio

[21] Appl. No.: 219,415

[22] Filed: Jul. 15, 1988

Related U.S. Application Data

[60] Division of Ser. No. 71,524, Jul. 7, 1987, Pat. No. 4,783,471, which is a continuation of Ser. No. 867,122, May 30, 1986, abandoned, which is a continuation-in-part of Ser. No. 751,419, Jul. 2, 1985, abandoned.

[51] Int. Cl.$^4$ ............................................. A61K 31/445
[52] U.S. Cl. ...................................... 514/317; 514/331
[58] Field of Search ................ 514/317, 331; 546/241

[56] References Cited

U.S. PATENT DOCUMENTS

| | | | |
|---|---|---|---|
| 3,029,244 | 4/1962 | Lyle et al. | 546/221 |
| 3,037,986 | 6/1962 | Langis | 546/241 |
| 3,576,810 | 4/1971 | Duncan | 546/225 |
| 3,632,767 | 1/1972 | Gray | 546/225 |
| 3,852,455 | 12/1974 | Carr | 546/241 |
| 4,101,663 | 7/1978 | Helsley et al. | 546/225 |
| 4,110,331 | 8/1978 | Pettersson | 546/225 |
| 4,430,334 | 2/1984 | Wick et al. | 514/317 |
| 4,569,941 | 2/1986 | Suh et al. | 514/317 |

*Primary Examiner*—Frederick E. Waddell

[57] ABSTRACT

This invention relates to a new class of compounds having important biochemical and pharmacological properties. More particularly, this invention relates to N-aralkyl piperidinemethanol derivatives which are potent and selective inhibitors of the binding of serotonin at the 5HT$_2$ receptor site, and to the processes for their preparation and use.

9 Claims, No Drawings

NOVEL CHEMICAL COMPOUNDS

This is a division of Ser. No. 71,524, filed July 7, 1987 which is now U.S. Pat. No. 4,783,471, which was a continuation of application Ser. No. 867,122, filed May 30, 1986 which is now abandoned, which is a continuation-in-part of application Ser. No. 751,419 filed July 2, 1985 which is now abandoned.

This invention relates to a new class of compounds having important biochemical and pharmacological properties. More particularly, this invention relates to N-aralkyl piperidinemethanol derivatives which are potent and selective inhibitors of the binding of serotonin at the $5HT_2$ receptor site, and to the processes for their preparation and use.

The compounds of this invention are represented by the formula

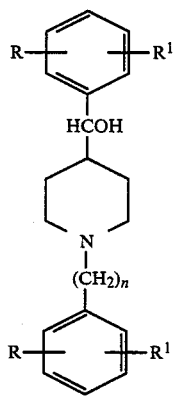

I their optical isomers and mixtures thereof, the pharmaceutically acceptable salts thereof, wherein n is 2, 3 or 4 and each R and $R^1$ independently represents hydrogen, $C_{1-6}$ alkyl, halogen, trifluoromethyl, hydroxy, $C_{1-6}$ alkoxy, or amino.

Representative of the R and $R^1$ substituents for $C_{1-6}$ alkyl are methyl, ethyl, propyl, isopropyl, n-butyl, t-butyl, pentyl, hexyl, cyclopropyl, cyclopentyl with methyl and ethyl being preferred. All halogens are embraced with fluoro and chloro being preferred. Representative $C_{1-6}$ alkoxy substituents are methoxy, ethoxy, isopropoxy and such of the aforementioned alkyl groups attached thru an oxygen. In those instances wherein R or $R^1$ are other than hydrogen, the substituents may be located at any position, (ortho, meta or para) but para is preferred for monosubstituted phenyl moieties. The 2,3-, 2,4-, 2,5-, 3,4-, or 3,5- disubstituted phenyl moieties are embraced herein. The compounds of Formula I contain an asymmetric carbon atom and thus exist in optically isomeric forms. Embraced within this invention are the individual optical isomers and the mixtures thereof. Such mixtures may readily be separated by standard techniques well known in the art.

The preparation of the compounds of this invention may be achieved by standard chemical reactions analogously known in the art. In general, it is preferred to N-alkylate an appropriately $R,R^1$-substituted phenyl 4-piperidinemethanone to produce a $R,R^1$ phenyl-[1-$R,R^1$-phenylalkyl-4-piperidinyl] methanone intermediate, which intermediate is then chemically reduced to the desired product (I). Alternately the 4-piperidinones may be chemically reduced to their alcohols and these intermediates may be N-alkylated to the desired products (I). The chemical reduction of the ketones to their corresponding alcohols may be effected by standard reduction procedures such as by catalytic hydrogenation or metal hydride reduction preferably with sodium or potassium borohydride. In either case in those instances wherein any R or $R^1$ substituent represents a reactive hydroxy group then such group should first be protected (using such standard protecting groups as acetate, trifluoroacetate, benzyloxy, benzyloxycarbonyl and the like) and then, following the foregoing N-alkylation-reduction reactions, the protecting group is removed. Standard techniques for protecting and deprotecting hydroxy functions are well known in the art. Analogously in those instances wherein any R group represents an amino moiety, it is preferred to prepare the appropriate nitro analog and, as a last step, reduce the nitro group to the desired amino moiety. The foregoing reactions may conveniently be depicted by the following reaction scheme.

Reaction Scheme A

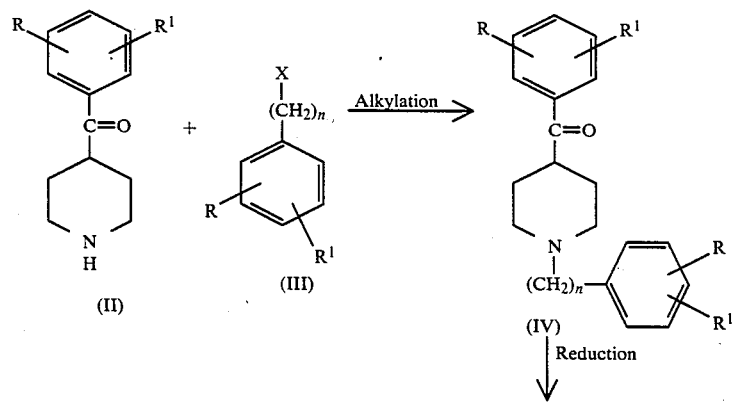

Reaction Scheme A

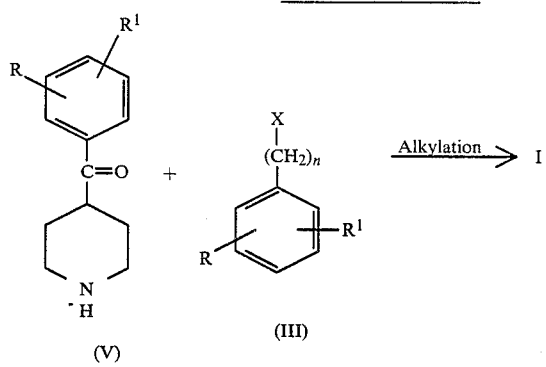

wherein X is a suitable leaving group (e.g., halide, tosylate or other functional equivalent thereof) and n, R and $R^1$ are as defined for compounds of Formula I.

The N-alkylation procedures are effected by reacting about equimolar quantities of the N-alkylating reactants (III) with an appropriately substituted 4-piperidinemethanol (II) or 4-piperidinylmethanone (V), in a suitable solvent, in the presence of an acid acceptor (e.g., the carbonates or bicarbonates of potassium or sodium, or an excess of the piperidine reactant), optionally with a small amount of potassium iodide being present. Suitable solvents are toluene, xylene, chlorobenzene, N,N-dimethylformamide, N,N-dimethylacetamide, ketones (acetone, butanone, MIBK, cyclohexanone, cyclopentanone, etc.) and alcohols (ethanol, propanol, butanol, etc.) The reaction mixture is heated over a wide range of temperatures (50 °C.–180° C.) although it is preferred to heat at reflux temperatures of the reaction mixture. The reaction is continued until completed, generally a period of several hours to several days.

After completion of the reaction, the reaction mixture is filtered, the product optionally converted to its mineral or organic acid salt and the desired product is recrystallized by techniques well-known in the art. Suitable solvents for recrystallization are methanol, ethanol, isopropanol, butanone, acetone, ethyl acetate, diethylether and the like.

The intermediate $R,R^1$-substituted phenyl 4-piperidyl ketones (II) used in the preparation of the compounds of Reaction Scheme A may be prepared by a Friedel-Craft reaction of benzene or a $R,R^1$ substituted benzene with isonipecotic acid chloride HCl or N-(trifluoroacetyl) isonipecotic trifluoroacetic anhydride followed by aqueous potassium carbonate hydrolysis in the latter case. Reaction of a substituted phenyl Grignard reagent with 4-cyanopiperidine (prepared by hydrolyzing N-trifluoroacetl-4-cyanopiperidine) will also yield the intermediate ketones.

Alternative methods of synthesis of the compounds of this invention include the reactions of either a R, $R^1$-phenylmanesium halide or a R, $R^1$-substituted phenyl lithium reactant with 1-(ω-R,$R^1$-phenyl alkyl)-4-piperidine carboxaldehyde. Another alternative procedure includes the catalytic hydrogenation of an alpha-(R,$R_1$,phenylmethanol)-1-(R,$R^1$-phenylalkyl)-pyridinium halide, or its ketone analog, to the desired product. Still another method is the chemical reduction of a R,$R^1$-phenyl[-1-([2-R, $R^1$- phenacyl]-4-piperidinyl]-methanone to the desired products of this invention. For these foregoing reactions standard procedures well known in the art may be used in the preparation of the necessary intermediates as well as for the final step producing the desired products.

Having taught the general methods for the preparation of the compounds of this invention the following examples typify the preferred routes of preparation.

EXAMPLE 1

Alpha-Phenyl-1-(2-Phenylethyl)-4-Piperidinemethanol HCl

Step A: Phenyl[1-(2-phenylethyl)-4-piperidinyl]-methanone HCl. A reaction mixture containing phenyl(4-piperidinyl)methanone (20.5 g, 0.108 mol), $K_2CO_3$ (33.17 g, 0.18 mol), potassium iodide (0.2 g) and 2-bromoethyl benzene (22.2 g, 0.12 mol, 16.4 ml) in toluene (250 ml) was stirred at reflux temperature for 66 h. The reaction mixture was filtered and the filtrate concentrated to a residue which was dissolved in dry $Et_2O$ (500 ml) and treated dropwise with a solution of HCl (0.11 mol) in EtOAc. The resultant precipitate was recrystallized from EtOH:$CH_3OH$, 4:1 (500 ml) to give phenyl[1-(2-phenylethyl)-4-piperidinyl]-methanone hydrochloride, mp 258°–260° C.

Step B: A solution of phenyl[1-(2-phenylethyl)-4-piperidinyl]-methanone (11.0 g, 0.037 mol) in absolute EtOH (150 ml) was stirred at room temperature and treated portionwise with $NaBH_4$ (2.84 g, 0.075 mol) and was stirred overnight (16 h). The reaction mixture was concentrated at reduced pressure to give a residue which was partitioned between $CH_2Cl_2$ (250 ml) and 10% NaOH solution (100 ml). The aqueous layer was further extracted with $CH_2Cl_2$ (2×50 ml) and the combined extracts washed with saturated NaCl solution (100 ml) and dried over $MgSO_4$. The mixture was filtered and concentrated to give a solid (10 g) which was dissolved in dry $Et_2O$/EtOAc (1:1, 350 ml) and treated with HCl (0.034 mol) dissolved in EtOAc/$CH_3OH$ (3:1, 20 ml). The resultant precipitate was recrystallized twice from methanol/butanone to give phenyl-1-(2-phenyl-ethyl)-4-piperidinemethanol hydrochloride, mp 141°–143.5° C.

EXAMPLE 2

Alpha-Phenyl-1-(2-Phenylethyl)-4-Piperidinemethanol

A mixture of alpha-phenyl-4-piperidinemethanol (1.5 g, 7.8 mmol), 2-bromoethyl benzene (1.1 ml, 8.0 mmol) and potassium carbonate (1.1 g, 8.0 mmol) in dry DMF (20 ml) was heated at 80° C. over the weekend (60 h). The excess DMF was distilled off at reduced pressure and the residue was dissolved in ethyl acetate. The organic phase was washed with $H_2O$ (3×100 ml), saturated aqueous NaCl (1×100 ml), dried (MgSO$_4$), filtered and evaporated to give a pale yellow oil which eventually crystallized. After recrystallization from ethyl acetate-hexane, a white crystalline solid was obtained, mp 125°–128° C.

EXAMPLE 3

Alpha-Phenyl-1-(3-Phenylpropyl)-4-Piperidinemethanol

Step A: Phenyl [1-(3-phenylpropyl)-4-piperidinyl]-methanone hydrochloride. A solution of phenyl (4-piperidinyl)methanone (18.1 g, 0.096 mol) was dissolved in toluene (200 ml) containing 1-bromo-3-phenylpropane (21.9 g, 0.11 mol, 16.7 ml), K$_2$CO$_3$ (30.4 g, 0.22 mol) and KI (0.2 g) and was refluxed for 64 h. The reaction mixture was filtered and concentrated to give a light yellow oil. This material was dissolved in toluene/EtOAc (1:1) and treated with HCl (0.096 mol) dissolved in CH$_3$OH/EtOAc (2:5, 35 ml) to give a precipitate which was filtered off and recrystallized twice from EtOH/Et$_2$O (150 ml) to give phenyl[1-(3-phenylpropyl)-4-piperidinyl)-methanone hydrochloride, mp 199°–200° C.

Step B: To a stirred solution of phenyl1-(3-phenylpropyl)-4-piperidinyl]-methanone hydrochloride (6.8 g, 0.02 mol) in absolute ethanol (120 ml) was added sodium methoxide (1.08 g, 0.04 mol) followed by sodium borohydride (1.51 g, 0.04 mol). The reaction mixture was stirred for 72 h and then concentrated at reduced pressure to a solid residue. This material was stirred with aqueous 10% NaOH for 1 h and then extracted with toluene (2×50 ml). The extracts were washed with water and then saturated NaCl solution. The toluene solution was dried over MgSO$_4$, filtered and concentrated to a colorless oil. This material was dissolved in dry Et$_2$O (50 ml) and treated with a solution of HCl (0.02 mol) in CH$_3$OH/EtOAc (1:4, 12.5 ml). The resultant precipitate was dissolved in water, basified using 10% aqueous NaOH and extracted into toluene. The toluene solution was washed with saturated aqueous NaCl dried over MgSO$_4$, filtered and concentrated to a solid. This material was flash chromatographed on a 2.5×6.0 inch silica gel column, and eluted with CH$_3$OH/CH$_2$Cl$_2$ (1:9). The resultant fractions (7–9) eventually solidified and were recrystallized from acetone to give alpha-phenyl-1-(3-phenylpropyl)-4-piperidinemethanol, mp 87°–88° C.

EXAMPLE 4

Alpha-(4-Methylphenyl)-1-(2-Phenylethyl)-4-Piperidinemethanol HCl

Step A: (4-Methylphenyl)[1-(2-phenylethyl)-4-piperidinyl]-methanone HCl. A mixture containing 4-(methylphenyl)(4-piperidinyl)methanone (10.5 g, 0.052 mol), 2-bromoethyl benzene (11.1 g, 0.06 mol, 8.2 ml) in dry DMF (125 ml) was stirred at 100° C. for 23 h. The cooled reaction mixture was poured into H$_2$O (600 ml) and extracted with toluene (4×200 ml). The extracts were washed with H$_2$O (2×100 ml) saturated aqueous NaCl (100 ml) and dried over MgSO$_4$. The mixture was filtered and the filtrate concentrated to a solid residue which was dissolved in dry Et$_2$O and filtered. The filtrate was treated with a solution of HCl (0.052 mol) in CH$_3$OH/EtOAc (9:20, 29 ml). The mixture was cooled and filtered to give a light tan powder. The solid was recrystallized twice from EtOH/Et$_2$O to give (4-methylphenyl)[1-(2-phenylethyl)-4-piperidinyl)-methanone hydrochloride, which contains 0.4 mol of water of hydration and melts at 261°–263° C.

Step B: A solution of (4-methylphenyl)[1-(2-phenylethyl)-4-piperidinyl]-methanone hydrochloride (9.5 g, 0.028 mol) in absolute ethanol (350 ml) was treated first by the addition of NaOCH$_3$ (1.62 g, 0.03 mol) and then, portionwise, with sodium borohydride (2.27 g, 0.06 mol) and stirred at room temperature for 18 h. The reaction mixture was concentrated to a solid and stirred with 10% aqueous NaOH. The mixture was extracted with CH$_2$Cl$_2$ (3×50 ml). The CH$_2$Cl$_2$ solution was washed with water and then saturated NaCl solution, and dried over Na$_2$SO$_4$. After filtering off the Na$_2$SO$_4$, the filtrate was concentrated to a solid. This material was dissolved in EtOAc/Et$_2$O (1:1, 200 ml) and treated with a solution of HCl (0.023 mol) in CH$_3$OH/EtOAc (3:10, 13 ml). The resulting precipitate was twice recrystallized from butanone containing a small amount of CH$_3$OH to give alpha-(4-methylphenyl)-1-(2-phenylethyl)-4-piperidinemethanol hydrochloride, mp 181°–183° C.

EXAMPLE 5

Alpha-(4-Methoxyphenyl)-1-(2-Phenylethyl)-4-Piperdinemethanol HCl

Step A: (4-Methoxyphenyl)[1-(2-phenylethyl)-4-piperidinyl]-methanone HCl. A reaction mixture containing 4-(methoxyphenyl)(4-piperidinyl)methanone (10.3 g, 0.047 mol), 2-bromoethylbenzene (9.57 g, 0.052 mol, 7.1 ml) and K$_2$CO$_3$ (15.2 g, 0.11 mol) in dry DMF (100 ml) was stirred at 90° for 65 h. The cooled reaction mixture was poured into H$_2$O (500 ml) and extracted with toluene (3×100 ml). The extracts were washed with H$_2$O, saturated aqueous NaCl solution and dried over MgSO$_4$. The mixture was filtered and the filtrate concentrated to a residue which was triturated with hexane and filtered. The resulting precipitate (0.022 mol) was dissolved in dry Et$_2$O and treated with a solution of HCl (0.022 mol) in CH$_3$OH/EtOAc (2:5, 14 ml) to give a precipitate which was twice recrystallized from EtOH/Et$_2$O, to give (4-methoxyphenyl)[1-(2-phenylethyl)-4-piperidinyl]-methanone hydrochloride, mp 238.5°–239.5° C.

Step B: A solution of (4-methoxyphenyl)[1-(2-phenylethyl)-4-piperidinyl]-methanone hydrochloride (3.5 g, 9.7 mmol) in absolute EtOH (75 ml) was treated with sodium methoxide (0.53 g, 9.7 mmol) followed by sodium borohydride (1.08 g, 20 mmol) and the mixture stirred for 42 h at room temperature. The reaction mixture was filtered and the filtrate concentrated to a solid residue which was dissolved in absolute Et$_2$O and treated with HCl (9.7 mmol) dissolved in CH$_3$OH/EtOAc (1:3, 8 ml). The resulting precipitate was filtered and recrystallized from CH$_3$OH/Et$_2$O to give alpha-(4-methoxyphenyl)-1-(2-phenylethyl)-4-piperidinemethanol hydrochloride, mp 162.5°–164° C.

EXAMPLE 6

Alpha-[4-(1-Methylethyl)Phenyl]1-(2-Phenylethyl Piperidinyl]-Methanol HCl

Step A: [4-(1-methylethyl)phenyl][1-(2-phenylethyl)-piperidinyl]-methanone HCl. A solution of [4-(1-methylethyl)phenyl](4-piperidinyl)-methanone (43 g, 0.19 mol) in toluene (500 ml) was treated with 2-bromoethylbenzene (37 g, 0.2 mol), K$_2$CO$_3$ (25 g, 0.18 mol), KHCO$_3$ (25 g, 0.25 mol) and potassium iodide (0.1 g) and the mixture heated on a steam bath for 68 h. The reaction mixture was filtered and the filtrate treated with ethereal hydrogen chloride until acid to congo red indicator paper. The resultant precipitate was filtered off and recrystallized twice from CH₃OH/butanone to give [4-(1-methylethyl)phenyl][1-(2-phenylethyl)-piperidinyl-methanone hydrochloride, mp 251°–253° C. By following the sodium borohydride reduction procedure of the foregoing example there is obtained the desired product of this example.

EXAMPLE 7

Alpha-(3,5-Dimethylphenyl)-1-(2-Phenylethyl) Alpha-4-Pieridinemethanol

Step A: (3,5-Dimethylphenyl)[1-(2-phenylethyl)-4-piperidinyl]-methanone HCl. A solution of 5-bromo-mxylene (22.3 g, 0.12 mol) in dry THF (50 ml) was added under N₂ to an oven dried 1 L round bottom flask containing Mg turnings (3.0 g, 0.12 mol) and a crystal of I₂ covered with dry THF (50 ml) at a rate such that the THF gently refluxed once the reaction had commenced. After the addition was complete, the mixture was stirred for 1 h at room temperature. At this time the Grignard solution was diluted to 500 ml with dry THF and 4-cyano-1-(2-phenylethyl)piperidine (15.0 g, 0.12 mol) in dry THF (50 ml) was added over a period of 15 min. Dry toluene (250 ml) was added and the mixture refluxed while THF was distilled off until a reaction temperature of 85° C. was reached. The mixture was refluxed at this temperature overnight (16 h). It was then cooled in an ice bath and 1N H₂SO₄ (200 ml) was added dropwise with vigorous stirring. When the addition was complete, the mixture was warmed to room temperature and stirred an additional 3 h. The aqueous phase was separated and washed twice more with toluene (200 ml) before it was basified with aqueous 2N NaOH and extracted with Et₂O (3×200 ml). The extract was washed with saturated aqueous NaCl (1×250 ml), dried (MgSO₄), filtered and evaporated to give a yellow oil. This oil was distilled (Kugelrohr) to give a yellow glass which crystallized upon standing. This material was recrystallized from ether to give a white crystalline powder, mp 76°–78° C.

The hydrochloride salt was prepared by adding the free base to a cold methanol solution containing one equivalent of HCl. This solution was evaporated to dryness and the residue recrystallized from methanol-butanone to give fluffy white crystals, mp 211°–214° C.

Step B: To a solution of (3,5-dimethylphenyl)[1-(2-phenylethyl)-4-piperidinyl]-methanone (21.5 g, 66.9 mmol) in methanol (300 ml) cooled in an ice bath was added portionwise with stirring sodium borohydride (2.53 g, 66.9 mmol). The reaction was allowed to warm to room temperature and stirred overnight (16 h). This mixture was evaporated and the residue stirred in Et₂O, washed with H₂O (3×100 ml), saturated aqueous NaCl (1×100 ml), dried (MgSO₄), filtered and evaporated to give a light yellow solid. This solid was recrystallized from butanone to give a white crystalline solid, mp 150°–154° C.

EXAMPLE 8

1-(2-Phenylethyl)-Alpha-[3-(Trifluoromethyl) Phenyl]-4-Piperidinemethanol

Step A: [1-(2-Phenylethyl)-4-piperidinyl][3-(trifluoromethyl)-phenyl]-methanone HCl. A solution of 3-bromobenzotrifluoride (17 ml, 0.12 mol) in dry THF (50 ml) was added under N₂ to an oven dried 1 L round bottom flask containing Mg turnings (3.0 g, 0.12 mol) and a crystal of I₂ covered with dry THF (50 ml) at a rate such that the THF gently refluxed once the reaction had commenced. After the addition was complete, the mixture was stirred for 1 h at room temperature. At this time the Grignard solution was diluted to 500 ml with dry THF and 4-cyano-1-(2-phenylethyl)piperidine (15.0 g, 0.12 mol) in dry THF (50 ml) was added over a period of 15 min. Dry toluene (250 ml) was added and the mixture refluxed while THF was distilled off until a reaction temperature of 85° C. was reached. The mixture was refluxed at this temperature overnight (16 h). It was then cooled in an ice bath and 1N H₂SO₄ (200 ml) was added dropwise with vigorous stirring. When the addition was complete, the mixture was warmed to room temperature and stirred an additional 1 h. The aqueous phase was separated and washed twice more with toluene (200 ml) before it was basified with aqueous 2N NaOH and extracted with Et₂O (3×200 ml). The extract was washed with aqueous saturated NaCl (1×250 ml), dried (MgSO₄), filtered and evaporated to an orange oil. This oil was distilled (Kugelrohr) to give a yellow glass (bp 120°–130° C., 1 mm Hg) which crystallized upon standing. This material was recrystallized from Et₂O to give white needles, mp 70°–73° C.

The hydrochloride salt was prepared by adding a solution of free base in methanol to a cold methanol solution containing one equivalent of HCl. This solution was evaporated to dryness and the residue recrystallized from methanol-butanone to give a white crystalline solid, mp 248°–251° C.

Step B: To a solution of [1-(2-phenylethyl)-4-piperidinyl][3-(trifluoromethyl)-phenyl]-methanone (2.8 g, 7.75 mmol) in methanol (50 ml) cooled in an ice bath was added portionwise sodium borohydride (0.3 g, 7.75 mmol). The reaction was allowed to warm to room temperature and stirred an additional 4 h. The mixture was evaporated and the residue extracted with Et₂O, washed with H₂O (3×100 ml), saturated aqueous NaCl (1×100 ml), dried (Mg SO₄), filtered and evaporated to give a white solid. This solid was recrystallized from ether-hexane to give white needles, mp 143°–147° C.

EXAMPLE 9

Alpha-(2,3-Dimethoxyphenyl)-1-(2-Phenylethyl)-4-Piperidinemethanol HCl

Step A: 1-(2-Phenylethyl)piperidine-4-carboxaldehyde. To a solution of 4-cyano-1-(2-phenylethyl)piperidine (6.5 g, 30.3 mmol) in dry toluene (100 ml) cooled in an ice bath was added dropwise 43 ml (43 mmol) of 1M diisobutylaluminum hydride in hexane. After the addition was complete, the mixture was warmed to room temperature and stirred overnight (16 h). Methanol was added to decompose any unreacted reagent and H₂O was added with vigorous stirring. The gelatinous aluminum salts were removed by filtration through Celite and the filtrate extracted with toluene (2×100 ml). The extracts were combined, washed with saturated aqueous NaCl, dried (MgSO₄) filtered and evaporated to give a clear oil. This oil was flash chromatographed on silica gel using acetone as eluent to give product as a clear oil, which was used without further purification.

Step B: To a solution of veratrole (2.5 ml, 19.6 mmol) in dry THF (150 ml) cooled to 0° C. was added 13 ml (20.7 mmol) of 1.6 M n-butyllithium dropwise. This mixture was kept at 0° C. for another 5 h before it was cooled to −45° C. and 1-(2-phenylethyl)piperidine-4- carboxaldehyde (3.6 g, 16.6 mmol) in dry THF (10 ml) was added dropwise. The mixture was kept at −45° C. for 1 h before it was allowed to warm to room temperature and stirred overnight (16 h). The reaction mixture was poured into 5% aqueous NH4Cl, extracted with Et2O (3×100 ml), dried (MgSO4), filtered and evaporated to an orange oil.

The hydrochloride salt was prepared by adding a solution of the free base in methanol to a cold methanol solution containing one equivalent of HCl. This solution was evaporated to give a foam which crystallized from a vigorously stirred acetone-hexane solution. Two recrystallizations from methanol-butanone gave pale orange crystals, mp 182°–185° C.

EXAMPLE 10

Alpha-(3,4-Dichlorophenyl)-1-(2-Phenylethyl)-4-Piperidinemethanol Hydrochloride

Step A: (3,4-Dichlorophenyl)[1-(2-phenylethyl)-4-piperidinyl]-methanone HCl. A solution of 1-bromo-3,4-dichlorobenzene (10.0 g, 44.2 mmol) in dry THF (50 ml) was added under N2 to an oven dried 1 L round bottom flask containing Mg turnings (1.2 g, 49.4 mmol) and a crystal of I2 covered with dry THF (50 ml) at a rate such that the THF gently refluxed once the reaction had commenced. After the addition was completed the mixture was stirred for 1 h at room temperature. At this time the Grignard solution was diluted to 500 ml with dry THF and 4-cyano-1-(2-phenylethyl)piperidine (9.5 g, 44.2 mmol) in dry THF (50 ml) was added over a period of 15 min. Dry toluene (250 ml) was added and the mixture refluxed while THF was distilled off until a reaction temperature of 80° §was reached. The mixture was refluxed at this temperature overnight (16 h). It was then cooled in an ice bath and 1N H2SO4 (200 ml) was added dropwise with vigorous stirring. When this addition was completed, the mixture was warmed to room temperature and stirred an additional 3 h. The aqueous phase was separated and washed twice more with toluene (200 ml), basified with aqueous 2N NaOH and extracted with Et2O (3×200 ml). The extract was washed with saturated aqueous NaCl (1×250 ml), dried (MgSO4), filtered and evaporated to give an orange solid. This solid was flashed chromatographed on silica gel using 20% acetone-dichloromethane as eluent and the resultant product triturated with Et2O to give a light orange solid.

The hydrochloride salt was prepared by adding the free base to a cold methanol solution containing one equivalent of HCl. This solution was evaporated to dryness and the residue recrystallized from methanol-butanone to give a white solid, mp 238°–242° C. with decomposition.

Step B: To a solution of (3,4-dichlorophenyl)[1-(2-phenylethyl)-4-piperdinyl]-methanone (1.9 g, 5.2 mmol) in sodium borohydride (0.6 g, 15.9 mmol). The reaction was allowed to warm to room temperature and stirred an additional 4 h. The mixture was evaporated and the residue stirred in Et2O, washed with H2O (3×100 ml), saturated aqueous NaCl (1×100 ml), dried (MgSO4), filtered and evaporated to give a white solid.

The hydrochloride salt was prepared by adding the free base to a cold methanol solution containing one equivalent of HCl. This solution was evaporated to give a pale yellow foam which crystallized from a vigorously stirred acetone-hexane solution. Recrystallization from methanol-butanone gave a white solid, mp 161°–164° C.

In a similar manner, by substantially following the teachings of the foregoing examples substituting the appropriate reactants there may be produced the following compounds.

(4-fluorophenyl)[1-(2-phenethyl)-4-piperidinyl]methanol.

Alpha-phenyl-1(4-Phenylbutyl)-4piperidinyl]methanol,

Alpha-(3,4-dimethoxyphenyl)[1-(2-Phenylethyl)-4piperidinyl]methanol,

Alpha-phenyl[1-(4-aminophenylethyl)-4-piperidinyl methanol,

Alpha-phenyl[1-(4-methoxyphenylethyl)]-4-piperidinyl methanol,

Alpha-(4-methoxyphenyl)-[1-(4-methoxyphenylethyl)]-4-piperidinyl methanol,

Alpha-(2,3-dimethoxyphenyl)-[1-(4methoxyphenylethyl)]-4-piperidinyl methanol,

Alpha-phenyl[1-(4-methylphenylethyl]-4-piperidinyl methanol,

Alpha-phenyl[1-(4-fluorophenylethyl)]-4-piperidinyl methanol,

Alpha-(4-hydroxyphenyl)-[1-(2-phenylethyl]-4piperidinyl methanol,

Alpha-(3,4-dihydroxyphenyl)-[1-(2-phenylethyl]-4piperidinyl methanol,

The compounds of this invention have very interesting biochemical and pharmacological activities. The compounds (I) are potent and selective serotonin antagonists in that, at relatively low doses, they inhibit the binding of serotonin at the5HT2 receptor sites with little, if any, inhibition of the binding of serotonin at the 5HT1 receptor sites. Further, since it has been reported that the receptor subserving the serotonin vasoconstriction is of the 5HT2 subtype, the serotonin antagonism at the 5HT2 receptor sites of the compounds of this invention will also be useful in the treatment of such serotonin-mediated disease states as anorexia nervosa, variant angina, Raynaud's phenomena and coronary vasospasms and in the prophylactic treatment of migraine.

Using standard laboratory in vitro and in vivo methodology, either alone or in comparison studies with known serotonin antagonists, it is readily seen that the compounds of this invention are potent serotonin antagonists at the 5HT2 receptor sites with virtually no activity at the 5HT1, adrenergic alpha-1, dopamine D-2 or muscarinic cholinergic receptors. By contrast with such well-known agents as ketanserin, methysergide and cyproheptadine such selectivity is, indeed, unique.

For example, utilizing anesthetized ganglion-blocked dog to assess alpha-adrenergic and sertoninergic blockade, it is to be found that the compounds of this invention antagonize the effects of a serotonin challenge in vivo (i.e., eliminated the pressor response to serotonin) and had no effect on the phenylephrine in vivo challenge thus demonstrating in vivo antagonism of the vascular effects of serotonin which is accompanied with little, if any, alpha-adrenergic receptor blocking activity. Ketanserin on the other hand will block both.

As with both ketanserin and cyproheptadine, the compounds of this invention were effective in blocking the effects of serotonin as measured in the standard 5-hydroxytryptophan-induced "head twitch" in vivo (mice) laboratory model. Further, contrary to findings with ketanserin, it is to be found that compounds of this invention have no significant anti-hypertensive activity in conscious spontaneously hypertensive rats (SHR).

However, in anesthetized spontaneously hypertensive rats, compounds of this invention produce a marked decrease in systolic blood pressure.

In summary, based on comparative studies it is expected that in view of their selectivity in exerting potent anti-serotonin effects, the compounds of this invention will exhibit an improved pharmacologically active profile over that exhibited by ketanserin (a compound being clinically evaluated for use in the treatment of cardiovascular diseases, e.g. hypertension, peripheral vascular disease, thrombotic episodes and cardiopulmonary emergencies) for, although a potent $5HT_2$ antagonist, it is non-selective in that it blocks H-1 and alpha-1 adrenergic receptors. Similarly, because of their numerous side effects the marketed serotonin antagonists methysergide and cyproheptadine have a less desirable pharmacological profile than that possessed by the compounds of this invention.

In addition the compounds of this invention exhibit topical anesthetic activity similar in effect to that of procaine, and they also exhibit an analgesic effect in the standard acetic-acid-induced writhing test.

The compounds (I) exert their serotonin antagonist-induced pharmacological activities at 1-10 mg/kg when parenterally administered and at 0.1-3 mp/kg when intravenously administered. On comparative bases it is expected that the compounds of this will exert their end-use therapeutic effects at 30-600 mg per day (on 70 kg body weight), this amount being administered in divided doses. In each specific instance, depending on the severity and type of disease state, the attending diagnostician will readily be able to determine the dosage and its frequency of administration.

Further, the compounds of this invention also exhibit significant anti-fibrillatory effects when tested according to standard laboratory techniques, said techniques being useful in the determination of anti-arrythmic properties. Thus, the compounds particularly, alpha-phenyl-1-(2-phenethyl)-4-piperidinemethanol (and its salts), are useful in the prevention and/or treatment of ventricular fibrillatory aberrations due to acute myocardial ischemia. Other arrhythmic conditions contemplated include ventricular tachycardia, atrioventricular nodal beats, auricular flutter, auricular fibrillation and premature ventricular contractions.

The compounds of this invention exert their anti-arrythmic pharmacological activities at 1-100 mg/kg when enterally administered and at 0.1-10 mg/kg when administered intravenously.

The compounds of this invention, as defined by Formula I, can be administered as such, or can be administered in the form of a composition comprising the active ingredient and any of the commonly used pharmaceutical carriers. These carriers must be compatible with the active ingredient, and can be either solid or liquid, therapeutically active or insert. By using such carriers, one can make these compositions in the form of tablets, capsules, powders, suppositories, oral suspensions, or syrups. The compositions can also be made in the form of sterile solutions which are suitable for injection. The compositions will contain from 1% to 95% by weight of active compound, and from 5% to 99% by weight of a suitable pharmaceutical carrier. These ranges, however, are not critical and can be varied as desired according to the circumstances.

A sterile solution suitable for injection is prepared by admixing from 0.5 to 5 parts by weight of the active ingredient, preferably in the form of its salt, and from 95 to 99.5 parts by weight of water or isotonic saline solution at a temperature and for time sufficient to dissolve the active ingredient. This solution is then sterilized by filtration or by the application of heat.

These injectable solutions can be prepared with a high concentration of active ingredient. The solution is then diluted to a desired concentration before it is used.

The compounds of Formula I can also be administered in the form of hard or soft gelatin capsules. These capsules are filled with the proper amount of active ingredient and solid filler, such as starch, gelatin, lactose, talc, stearic acid, or magnesium stearate. Such a capsule can contain from 5 to 50 milligrams of active material, thus providing a minimum dose of active ingredient in a form convenient for oral administration.

The compounds of Formula I, when mixed with a suitable carrier, can also be formulated as tablets. Such carriers must be compatible with the active ingredient and can be the carriers mentioned for use with capsules, or can be such binders or fillers as cornstarch, acacia, gelatin, or cellulosic materials. Generally, any of the tableting materials conventionally used in pharmaceutical practice can be employed if there is no incompatibility with the active ingredient.

The tablets are made by admixing the active ingredient, a suitable filler, a lubricant or mold-release agent, and a binder, and compressing the mixture in a conventional tableting machine into tablets of a preselected size. Preferably, each tablet will contain from 5 to 50 milligrams of active ingredient. The tablet can be scored so that they are easily broken. Optionally, the tablets can be coated with tablet-coating materials in order to make them more attractive and palatable. They can also have enteric coatings so that they will release their ingredients slowly and over a longer period.

The pharmaceutical carrier in such suspensions or syrups can be an aqueous vehicle such as an aromatic water, a syrup, or a pharmaceutical mucilage. Suitable aromatic waters include the following: Anise Water, N.F. (IX); Bitter Almond Water, N.F. (VIII); Camphor Water, N.F.; Cinnamon Water, U.S.P.; Fennel Water, N.F.; Peppermint Water, U.S.P.: Spearmint Water, N.F. (IX); Wintergreen Water, N.F. (IX); Suitable syrups include the following: Syrup (Simple Syrup), U.S.P.; Acacia Syrup, U.S.P.; Aromatic Eriodictyon Syrup, N.F.; Aromatic Rhubarb Syrup, N.F. (IX); Cacao Syrup, U.S.P.; Cherry Syrup, U.S.P.; Cinnamon Syrup, N.F. (IX); Citric Acid Syrup, U.S.P.; Compound Sarsparilla Syrup, N.F.; Compound White Pine Syrup, N.F.; Ginger Syrup, N.F. (IX); Glycyrrhiza (Licorice) Syrup, U.S.P.; Orange Syrup, U.S.P.; Orange Flower Syrup, N.F.; Raspberry Syrup, U.S.P.; Rhubarb Syrup, N.F. (IX); Tolu Balsam Syrup, U.S.P.; Wild Cherry Syrup, U.S.P. Suitable pharmaceutical mucilages include the following: Acacia (Gum Arabic), U.S.P.; Acacia Mucilage, U.S.P.; Tragacanth, U.S.P.; Tragacanth Mucilage, N.F. The pharmaceutical carrier in the suspensions or syrups can also be a hydroalcoholic vehicle, such as an elixir. Suitable elixirs include the following: Aromatic Elixir, U.S.P.; Red Aromatic Elixir, N.F.; Glycyrrhiza Elixir, N.F.; Iso-Alcoholic Elixir (Iso-Elixir), N.F. Coloring agents, tinctures, spirits and other adjuvants can be admixed with the composition if desired.

Typical formulations incorporating the compounds of Formula I are described below. These formulations are intended to be illustrative merely and no limitation is implied or intended.

TABLET FORMULATION

| Formula | Grams per 1000 tablets |
|---|---|
| Active Ingredient* | 20.0 |
| Lactose | 270.0 |
| Dicalcium phosphate, hydrous | 122.5 |
| Polyvinylpyrrolidone | 25.0 |
| Polyvinylglycol 1500 | 7.5 |
| Corn starch | 50.0 |
| Magnesium stearate | 5.0 |
|  | 500.0 |

*Title compound of example 1

Mix the active ingredient, the lactose and the dicalcium phosphate. Dissolve the polyethylene glycol and the polyvinylpyrrolidone in approximately 20 ml of water. Granulate the powder blend with the water solution, adding additional water if necessary, to produce a damp mass. Pass the wet granulation through a 12 mesh screen; spread on trays and air dry at 35° C. Blend the dry granules with the starch and the magnesium stearate. Compress into 500 mg tablets.

CAPSULE FORMULATION

| Formula | Grams per 1000 capsules |
|---|---|
| Active Ingredient* | 20.0 |
| Lactose | 378.0 |
| Magnesium stearate | 2.0 |
|  | 400.0 |

*Title compound of example 1

Blend the ingredients and fill into hard gelatin capsules.

ELIXIR FORMULATION

| Formula | Grams per 1000 liters |
|---|---|
| Active Ingredient* | 40.0 |
| Sugar | " 500.0 |
| Glycerin | " 200.0 |
| Compound orange spirit | ml 10.0 |
| Alcohol | ml 100.0 |
| Amaranth | ml 0.1 |
| Water, q.s. 1000.0 ml. |  |

*Title compound of example 1

Dissolve the active ingredient, the sugar, the glycerin and the ammranth successively in approximately 400 ml of water with the aid of heat. Cool the solution to room temperature. Dissolve the compound orange spirit in the alcohol and add the alcoholic solution to the elixir base. Add sufficient water to make the product measure 1000 ml and agitated until homogeneous. Clarify the elixir by passing it through an asbestos pad, using a filter aid if necessary.

INJECTION FORMULATION

| Formula | Grams per 1000 ampuls |
|---|---|
| Active Ingredient* | 110.0 |
| Water for injection, q.s. 1100.0 ml. |  |

*Title compound of example 1

Dissolve the active ingredient in the water for injection. Pass the solution through a sterile 0.45 micron membrane filter. Fill asceptically into ampuls (1.1 ml per ampul). Autoclave the sealed ampuls for 30 minutes under 20 p.s.i.g. stream pressure.

In order to achieve a satisfactory response, usually no more than 1 to 3 tablets or capsules as described above need be administered daily. The elixir described is usually administered in the amount of 1 to 3 teaspoons (5 cc.) per day while the usual injection dosage is 1 to 3 cc. per day. In severe or aggravated conditions, additional medicine may be administered.

As is true for most classes of compounds useful as therapeutic agents not all members have the same biological profile. In the present instance, on the basis of in vitro and in vivo studies, particularly when compared with prior art compounds, it is to be that when those compounds of Formula I wherein n is 2 such compounds are most preferred. When the R and $R^1$ groups of the phenalkyl moiety attached directly to the nitrogen atom of the piperidinal moiety are hydrogen and such compounds are preferred. Preferred substituents on the other phenyl moiety are 4-methoxy, 4-methyl, 3-trifluomethyl, 3,4-dichloro, 3,4-dimethoxy, 3,5-dimethyl and most preferred is when all R groups are hydrogen. Preferred specific compounds are:

alpha-phenyl-1-(2-phenethyl)-4-piperidine methanol,
alpha-phenyl-1-(3-phenpropyl)-4-piperidine methanol,
alpha-(4-methylphenyl)-1-(2-phenethyl)-4-piperidine methanol,
alpha-(4-methoxyphenyl)-1-(2-phenethyl)-4-piperidine methanol,
alpha-(3,5 dimethylphenyl)-1-(2-phenethyl)-4-piperidine methanol,
alpha-(3-(trifluoromethyl)phenyl)-1-(2-phenethyl)-4piperidine methanol,
alpha-(2,3-dimethoxyphenyl)-1-(2-phenethyl)-4-piperidine methanol, the first and last named compounds being most preferred.

We claim:

1. A method for the treatment of varient angina comprising administering to a patient in need thereof, by a suitable route of administration, an effective amount of a compound of the formula:

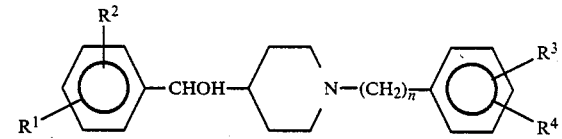

the optical isomers thereof, and the pharmaceutically acceptable salts thereof, wherein n is 2, 3, or 4, each of $R^1$, $R^2$, $R^3$, and $R^4$ is independently selected from hydrogen, halogen, trifluoromethyl, $C_{1-6}$ alkyl, $C_{1-6}$ alkoxy, hydroxy or amino.

2. The method of claim 1 wherein said compound is alpha-phenyl-1-(2-phenethyl)-4-piperidine methanol.

3. The method of claim 1 wherein said compound is alpha-phenyl-1-(3-phenpropyl)-4-piperidine methanol.

4. The method of claim 1 wherein said compound is alpha-(4-methylphenyl)-1-(2-phenethyl)-4-piperidine methanol.

5. The method of claim 1 where said compound is alpha-(4-methoxyphenyl)-(2-phenethyl)-4-piperidine methanol.

6. The method of claim 1 wherein said compound is alpha-(3,5-dimethylphenyl)-1-(2-phenethyl)-4-piperidine methanol.

7. The method of claim 1, wherein said compound is alpha-(3-(trifluoromethyl)phenyl-1-(2-phenethyl)-4-piperidine methanol.

8. The method of claim 1, wherein said compound is alpha-(2,3-dimethoxy)-1-(2-phenethyl)-4-piperidine methanol.

9. The method of claim 1, wherein said compound is alpha-(3,4-dichlorophenyl)-1-(2-phenylethyl)-4-piperidine methanol.

* * * * *